US005942191A

United States Patent [19]

Conway

[11] Patent Number: 5,942,191

[45] Date of Patent: Aug. 24, 1999

[54] BODY FLUID COLLECTION VESSEL HAVING REDUCED CAPACITY

[75] Inventor: Hugh T. Conway, Verona, N.J.

[73] Assignee: Becton, Dickinson and Company, Franklin Lakes, N.J.

[21] Appl. No.: 08/891,886

[22] Filed: Jul. 14, 1997

[51] Int. Cl.$^6$ .................................. B01L 3/14; A61B 5/14

[52] U.S. Cl. .................................................. 422/102

[58] Field of Search .................................. 422/58, 61, 72, 422/99, 101, 102, 103, 104; 220/4.24, 4.27

[56] References Cited

U.S. PATENT DOCUMENTS

| | | | |
|---|---|---|---|
| 3,615,222 | 10/1971 | Mead | 422/72 X |
| 3,807,955 | 4/1974 | Note, Jr. et al. | 422/102 X |
| 4,397,318 | 8/1983 | Burns | 128/673 |
| 4,830,217 | 5/1989 | Dufresne et al. | 422/102 |
| 5,384,096 | 1/1995 | Burns | 422/102 |
| 5,441,895 | 8/1995 | Jakubowicz et al. | 436/518 |
| 5,545,375 | 8/1996 | Tropsha et al. | 422/102 |

*Primary Examiner*—Jeffrey Snay
*Attorney, Agent, or Firm*—Arthur D. Dawson; Keith J. McWha

[57] ABSTRACT

A vessel useful for the collection of body fluid samples includes a first elongate tube defining an axis. The first tube has an open end with an inside diameter and a closed end section with an outside diameter. The first tube includes a receptacle therein for receiving a fluid sample that is accessible from open end. The vessel includes a second elongate tubes substantially identical to the first tube. The closed end section outside diameter is less than the inside diameter of the open end. The first tube closed end section is conjugately disposed in the open end of the second tube so that the first tube and the second tube are substantially axially aligned thereby forming a single article.

11 Claims, 5 Drawing Sheets

BODY FLUID COLLECTION VESSEL HAVING REDUCED CAPACITY

FIELD OF THE INVENTION

The present invention generally relates to the collection of body fluid samples and more particularly to body fluid collection devices.

BACKGROUND

Evacuated sample collection tubes have been in general usage in the United States for almost fifty years. Initially, as disclosed in U.S. Pat. No. 2,460,641 to Klienert, the sample collection tube was simply an evacuated glass test tube with a resilient stopper and intended for use in blood collection. As practitioners recognized the utility of these evacuated blood collection tubes, (trade named "Vacutainer" and available from Becton, Dickinson and Company, Franklin Lakes, N.J.) the tubes are now supplied with various additives already in them to prepare the blood specimen for a particular test. The tubes are also evacuated to selected less than atmospheric pressures to provide a preselected volume of blood drawn. The most widely used tubes are evacuated to provide a blood withdrawal volume between about four and one half milliliters to about ten milliliters.

Practitioners recognized the need for tubes with smaller capacity than the standard tubes and several alternative smaller tubes are available. U.S. Pat. No. 4,397,318 discloses a smaller tube termed a "microcollection tube" with a blood collector top. U.S. Pat. No. 5,384,096 also discloses a microcollection tube assembly that includes an adapter portion mounted on the closed end of the tube to facilitate handling of the small microcollection tube.

After the samples are collected in blood collection tubes, many of the tubes are used in some type of automated laboratory equipment ranging from centrifuges to automatic samplers and auto analyzers. Most of these automated devices are designed to accept the standard 13 mm×100 mm or 16 mm×100 mm tubes. Thus, the smaller microcollection tubes are not well suited to be used with much of the available automated equipment.

In an effort to address the handling problems, U.S. Pat. No. 5,384,096 discloses an adapter portion that serves to facilitate handling of the microcollection tube. Additionally, with the advent of blood collection tubes formed by injection molding of polymeric materials, standard sized tubes have been made available with reduced capacity reservoirs. These small capacity standard size tubes are molded with a large recess in the closed end. These tubes are more difficult to form by injection molding than a conventional "test-tube" shape and some of them do not feed particularly well through automated sampling equipment. The efficiency of forming and assembling different parts or molding more difficult shapes is less than the efficiency of forming more standard shaped blood collection tubes. Also, whenever there is device with more than one part, the manufacturing efficiency is reduced not only by the need to assemble the parts, maintain an inventory of separate parts as well as by the need for separate tooling and forming machinery for each part.

If a reduced capacity blood collection tube was available that only required one part, provided the desired sample draw capacity and additionally was compatible with automated sampling and analysis equipment, the art of blood sampling and analysis would be advanced. Such a blood collection tube is disclosed hereinbelow.

SUMMARY

A vessel of the present invention that is useful for the collection of body fluid samples includes a first elongate tube defining an axis. The first tube has an open end with an inside diameter and a closed end section with an outside diameter. The first tube includes a receptacle therein for receiving a fluid sample that is accessible from the open end. The vessel includes a second elongate tube substantially identical to the first tube. The closed end section outside diameter is less than the inside diameter of the open end. The first tube closed end section is conjugately disposed in the open end of the second tube so that the first tube and the second tube are substantially axially aligned thereby forming a single article.

The vessel of the invention allows practitioners of blood collection with tubes to have a device that is compatible with automated sample handling and automated analytical equipment that draws a sample only a fraction of the sample size required for the standard 13 mm×100 mm and 16 mm×100 mm tubes. The use of two substantially identical parts in the vessel of the invention allows the tube forming step to be substantially equally as efficient as the forming for a full-sized tube and, since the parts are the same, does not require a second injection molding tool, second injection molding press or a separate inventory of parts prior to assembly. The only additional step in assembling the vessel of the invention is mounting the closed end of the first tube into the open end of the second tube. Additionally, once the vessel of the invention is assembled from the two substantially identical first and second parts, since the assembled size is comparable to a standard tube, standard packaging and packaging equipment may be used in subsequent operations.

DETAILED DESCRIPTION

Figure 1:
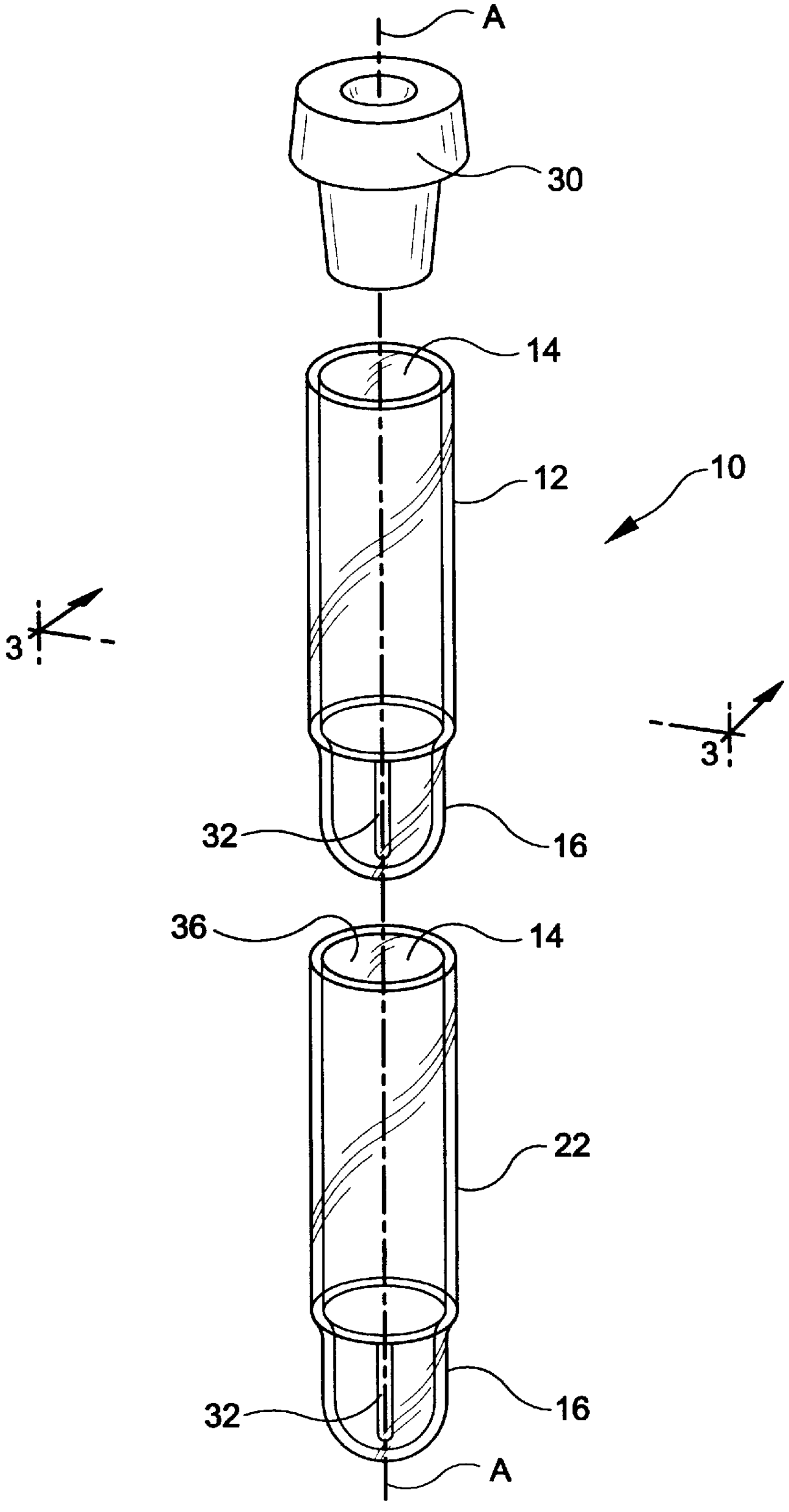
FIG. 1 is an exploded perspective view of the vessel of the invention.
Figure 2:
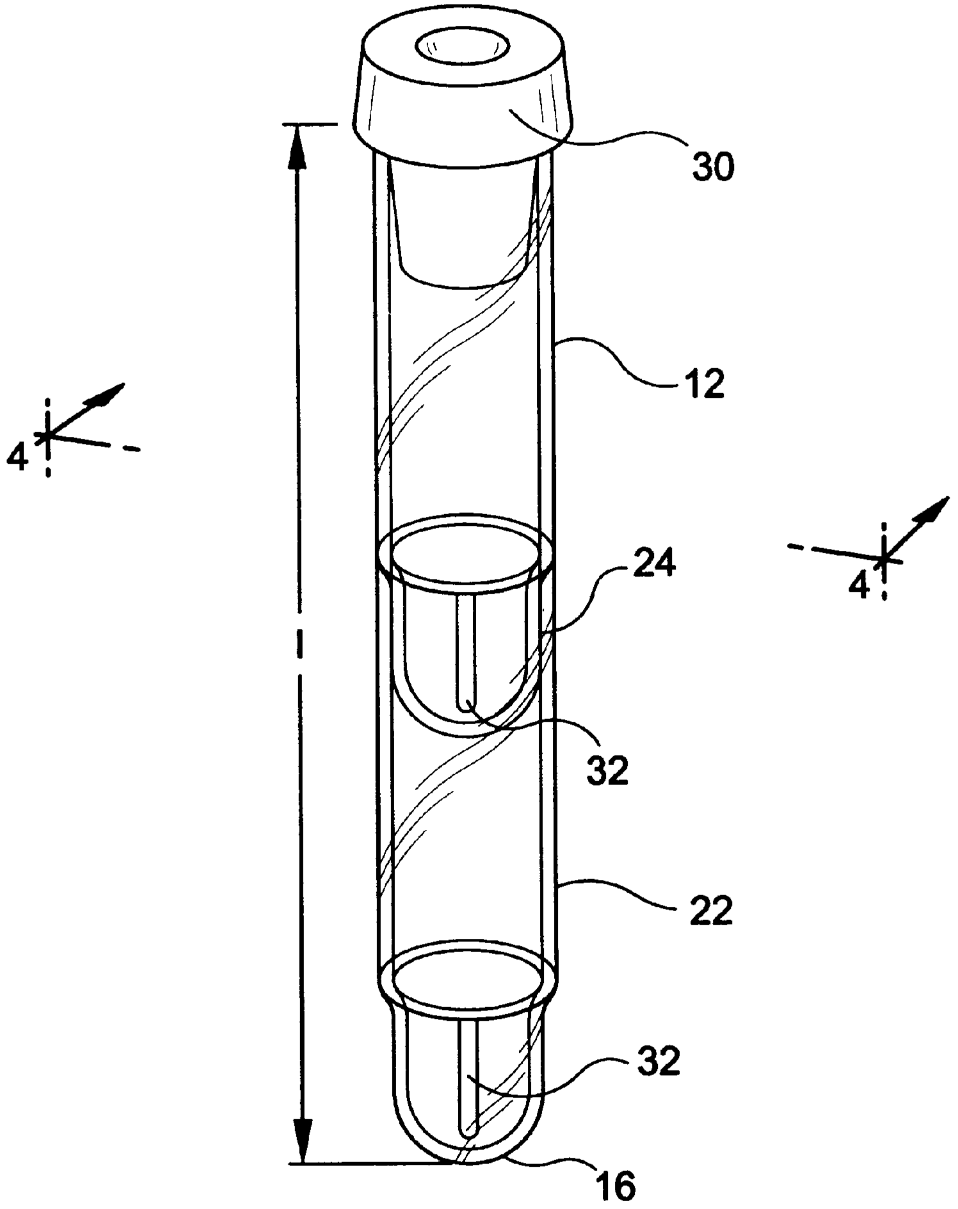
FIG. 2 is a perspective view of the vessel of the invention of FIG. 1.
Figure 3:
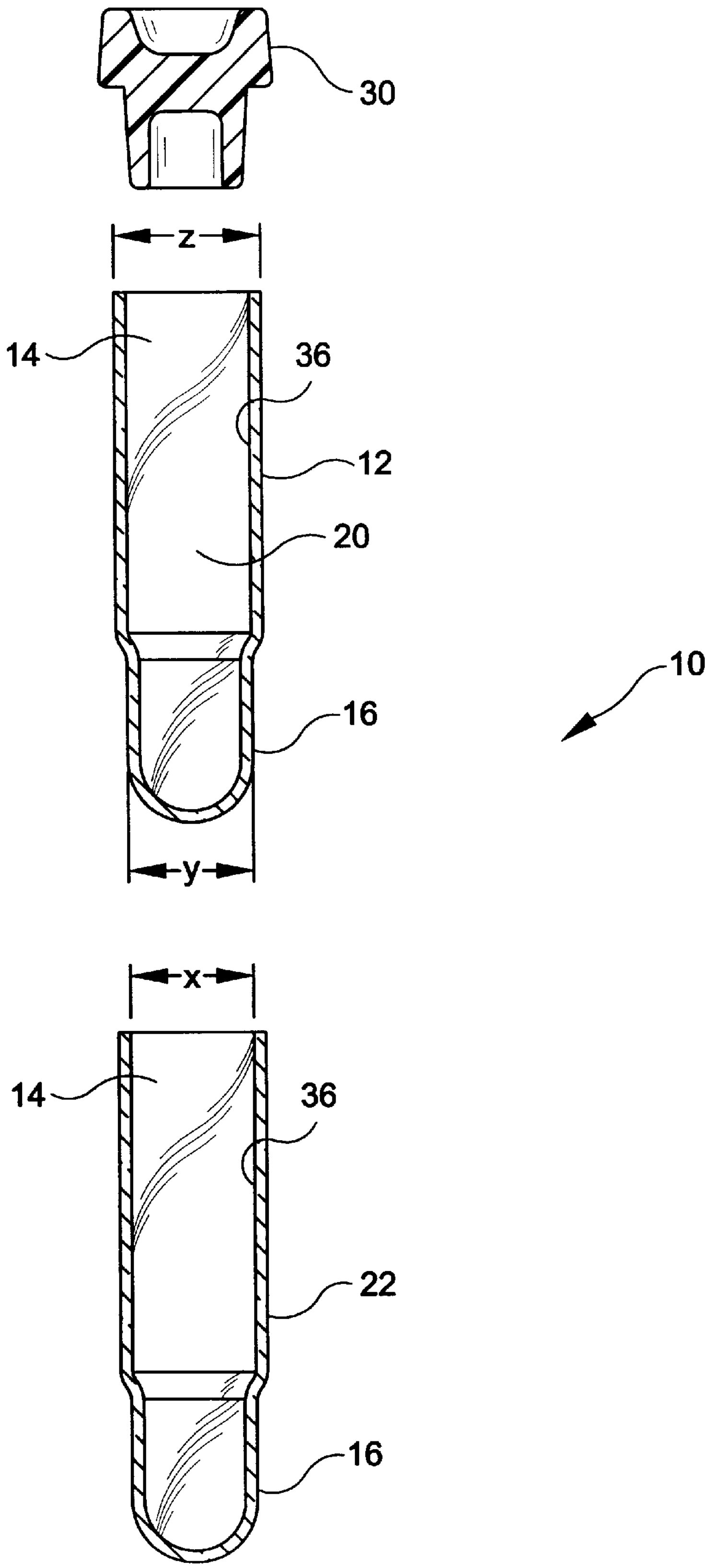
FIG. 3 is a cross-sectional view of the invention of FIG. 1 taken along the line 3—3.
Figure 4:
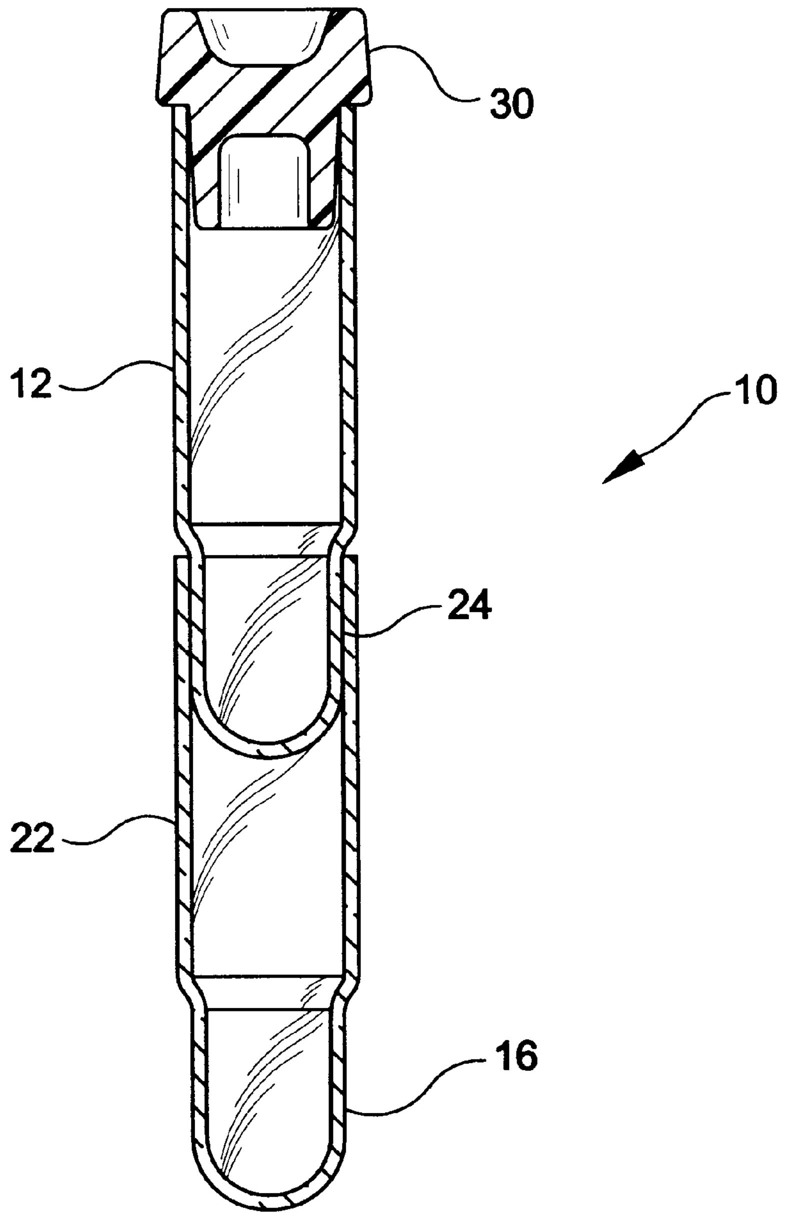
FIG. 4 is a cross-sectional view of the invention of FIG. 1 taken from FIG. 2 along the line 4—4.
Figure 5:
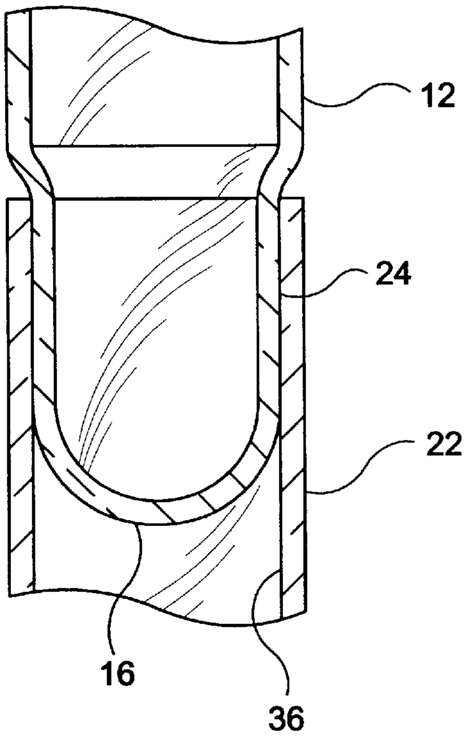
FIG. 5 is an enlarged schematic cross-sectional detail of the juncture between the first tube and the second tube taken from FIG. 4.

While this invention is satisfied by embodiments in many different forms, there is shown in the drawings and herein described in detail a preferred embodiment of the invention with the understanding that the present disclosure is to be considered exemplary of the principles of the invention and is not intended to limit the invention to the embodiment illustrated. The scope of the invention is measured by the appended claims and their equivalents.

Referring to FIGS. 1–6, a vessel 10 of the present invention that is useful for the collection and handling of body fluid samples includes a first elongate tube 12 defining an axis A. First tube 12 has an open end 14 with an inside diameter "x" and a closed end section 16 with an outside diameter "y". First tube 12 includes a receptacle 20 therein for receiving a fluid sample that is accessible from open end 14. Vessel includes a second elongate tube 22 substantially identical to first tube 12. Closed end section 16 outside diameter "y" is less than inside diameter "x" of open end 14.

First tube closed end section 16 is conjugately disposed in the open end 14 of second tube 22 so that first tube 12 and second tube 22 are substantially axially aligned thereby forming a single article.

Figure 6:
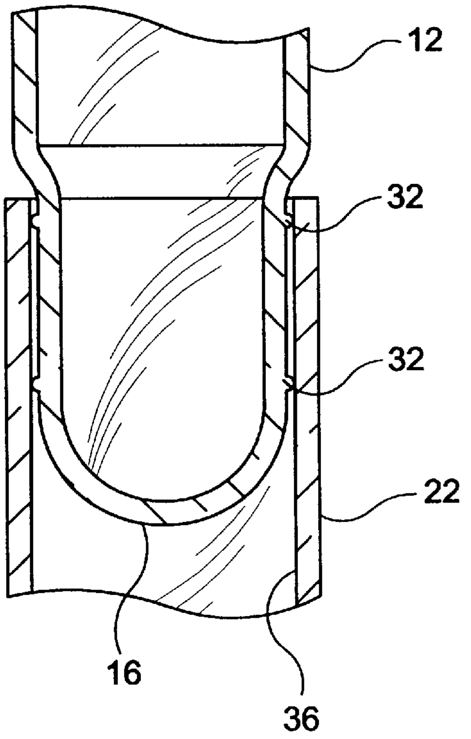
FIG. 6 is an enlarged schematic cross-sectional detail of an alternate embodiment of the juncture between the first tube and the second tube analogous to FIG. 5.

Preferably, vessel 10 is formed with first tube closed end section 16 fixedly attached into open end 14 of second tube 22. However, for particular applications, tube 12 may be removable from tube 22 or vessel 10 may be supplied unassembled. Preferably, first tube closed end section outside diameter "y" forms an interference fit when first tube closed end section 16 is disposed in open end 14 of second tube 22 thereby attaching, preferably fixedly, first tube 12 to second tube 22. Closed end section 16 may be fixedly attached into open end 14 of second tube 22 by a bond 24 formed by an adhesive, a thermal weld, a solvent weld an ultrasonic weld or any other method of forming a substantially permanent attachment between two parts formed form substantially the same material. Alternatively, as shown in FIG. 6, tube 12 closed end section 16 may be retained in second tube open end 14 by at least one protuberance 32 on an outside surface 34 disposed to engage an inner surface 36 of open end 16 of tube 22. Preferably, outside surface 34 includes two protuberances 32 on outside surface 34.

Since most conventional blood collection tubes are sized about 13 mm or 16 mm in diameter by about 100 mm in length, overall length "l" vessel 10 of the invention preferably is about 100 mm when first tube 12 and second tube 22 are assembled with first tube closed end section 16 is disposed in open end 14 of second tube 22 with an outside diameter "z" about 13 mm or 16 mm. This allows the tube of the invention to be handled by most automated tube handling, sampling and analytical equipment intended for conventional tubes. Although vessel 10 is preferably about 100 mm long, other lengths of the component tubes 12 and 22 may be preferred for particular applications and are considered within the scope of this disclosure.

Preferably, receptacle 20 in vessel 10 is evacuated to a selected pressure less than atmospheric pressure to facilitate drawing a preselected blood sample volume and is fitted with a closure 30, preferably a resilient closure for evacuated tube applications, that is sized to fit in open end 14 and maintain the selected pressure differential between atmospheric pressure and the receptacle. For particular applications, non-resilient closures may be preferred and are considered within the scope of this disclosure. Additionally, prior to evacuation of the receptacle, aliquots of aqueous or non aqueous additives may be introduced into receptacle. Preferably, the amount of these additives is proportional to the volume of receptacle 20 and the pressure differential selected to preselect the amount of blood sample drawn. Tubes of the invention are also useful for sample handling in general laboratory applications. For these applications, the tubes may be supplied unassembled and as specimens are prepared in them for analysis then fitted with closures and assembled.

Suitable materials for forming vessel 10 include, but are not limited to polyethyleneterephthalate, polycarbonate, polystyrene, polypropylene and the like. Preferably, first tube 12 and second tube 22 are formed by an injection molding process from polyethyleneterephthalate.

Since first tube 12 and second tube 22 are substantially identical, they may be formed on the same equipment. Only one injection molding press, one mold tool and one inventory of molded parts are required prior to assembly, thus maintaining the same efficiency of manufacture achieved with conventional molded blood collection tubes. The assembly step of tube 12 into tube 22 is relatively straight forward and does not require particularly sophisticated equipment. For assembly, tubes are axially aligned and then either pressed together for the interference fit tubes. Alternatively, when a bonding agent is selected, a bonding agent is applied and then the closed end of the first tube is placed into the open end of the second tube.

Once the first and the second tubes are assembled into vessel 10, conventional tube handling equipment for additive addition, evacuation, closure placement, labeling, packaging or any other operation for the standard 100 mm tubes is used. Thus, little additional cost for capital equipment is required to produce the tubes of the invention. The efficiency of manufacturing and using the tube of the invention is substantially similar to conventional tubes, with the added benefit to the art of facilitating a smaller volume sample collection. The efficiency to the practitioner of using the tube of the present invention is further advanced by the compatibility of the tube with most conventional automated sampling and analytical equipment.

What is claimed is:

1. A vessel useful for the collection of body fluid samples comprising:

a first tube defining an axis, said first tube having an open end with an inside diameter and a closed end section having an outside diameter, wherein said closed end section outside diameter is less than said inside diameter of said open end, and said first tube having a receptacle therein for receiving a fluid sample that is accessible from said open end;

a second tube, said second tube being substantially identical to said first tube and having an open end with an inside diameter and a closed end section having an outside diameter, wherein said closed end section outside diameter of said second tube is less than said inside diameter of said open end of said second tube, said first tube closed end section is fixedly attached into said open end of said second tube; and said first tube closed end section being conjugately disposed in said open end of said second tube so that said first tube and said second tube are substantially axially aligned thereby forming a single article.

2. The vessel of claim 1 wherein said first tube closed end section outside diameter forms an interference fit when said first tube closed end section is disposed in said open end of said second tube thereby fixedly attaching said first tube to said second tube.

3. The vessel of claim 1 wherein said first tube closed end section is fixedly attached into said open end of said second tube by a bond selected from the group consisting of an adhesive bond, a thermal weld, an ultrasonic weld and a solvent bond.

4. The vessel of claim 1 wherein said first tube and said second tube are sized so that when said first tube closed end section is disposed in the open end of said second tube, an overall length of said vessel is about one hundred millimeters.

5. The vessel of claim 1 further comprising a closure sized to fit in said open end of said first tube.

6. The vessel of claim 5 wherein said closure is formed from a resilient material.

7. The vessel of claim 6 wherein said receptacle is evacuated to a pressure less than atmospheric pressure and sealed with said resilient stopper.

8. The vessel of claim 1 wherein said first tube and said second tube are formed from a resin selected from the group consisting of polyethyleneterephthalate, polycarbonate, polystyrene and polypropylene.

9. The vessel of claim 1 wherein said first tube closed end section has an outside surface, said outside surface further includes at least one protuberance sized to provide an interference with said inside diameter of said open end of said second tube.

10. The vessel of claim 1 wherein said receptacle further includes at least one additive for treatment of said sample.

11. A vessel useful for the collection of body fluid samples comprising:

a first tube defining an axis and comprising an open end with an inside diameter and a closed end section having an outside diameter, wherein said closed end section outside diameter is less than said inside diameter of said open end, and said first tube having a receptacle therein for receiving a fluid sample that is accessible from said open end;

a second elongate tube being substantially identical to said first tube, comprising an open end with an inside diameter and a closed end section having an outside diameter, wherein said closed end section outside diameter of said second tube is less than said inside diameter of said open end of said second tube;

said first tube closed end section fixedly attached into said open end of said second tube;

said first tube and said second tube being sized so that when said first tube closed end section is disposed in the open end of said second tube, an overall length of said vessel is about 100 millimeters;

said receptacle being evacuated to a pressure less than atmospheric pressure and sealed with a resilient stopper; and said first tube closed end section being conjugately disposed in said open end of said second tube so that said first tube and said second tube are substantially axially aligned thereby forming a single article.

* * * * *